United States Patent
Florent

(10) Patent No.: US 9,070,205 B2
(45) Date of Patent: Jun. 30, 2015

(54) COMBINED DEVICE-AND-ANATOMY BOOSTING

(75) Inventor: Raoul Florent, Ville Davray (FR)

(73) Assignee: Koninklijke Philips N.V., Eindhoven (NL)

( * ) Notice: Subject to any disclaimer, the term of this patent is extended or adjusted under 35 U.S.C. 154(b) by 1067 days.

(21) Appl. No.: 13/121,961

(22) PCT Filed: Oct. 6, 2009

(86) PCT No.: PCT/IB2009/054363
§ 371 (c)(1),
(2), (4) Date: Apr. 28, 2011

(87) PCT Pub. No.: WO2010/044001
PCT Pub. Date: Apr. 22, 2010

(65) Prior Publication Data
US 2011/0216092 A1  Sep. 8, 2011

(30) Foreign Application Priority Data
Oct. 13, 2008  (EP) .................... 08166463

(51) Int. Cl.
*G06K 9/00* (2006.01)
*G06K 9/32* (2006.01)
(Continued)

(52) U.S. Cl.
CPC .............. *G06T 5/50* (2013.01); *A61B 2019/502* (2013.01); *A61B 2019/5238* (2013.01);
(Continued)

(58) Field of Classification Search
USPC ............ 382/128, 164, 173, 254, 276; 348/50, 348/77, E07.085, E13.074; 345/634; 600/437, 440, 443, 450; 250/370.11
See application file for complete search history.

(56) References Cited

U.S. PATENT DOCUMENTS 5,976,088 A * 11/1999 Urbano et al. ................ 600/443
7,488,948 B2 * 2/2009 Ishii et al. ................ 250/370.11
(Continued)

FOREIGN PATENT DOCUMENTS

WO   2005079492 A2   9/2005
WO   2006042198 A2   4/2006
(Continued)

OTHER PUBLICATIONS

By Pierfrancesco Agostoni et al. "Bifurcation Stenting With a Dedicated Biolimus-Eluting Stent: X-Ray Visual Enhancement of the Final Angiographic Result With "Stentboos Substract Catherization and Cardiovascular Interventions; vol. 70, Mar. 21, 2007, pp. 233-236, XP002609152; Retrieved from the Internet:; URL:http://onli neli brary.wiley.com/doi/I0.1002ccd.21096/pdf; [retrieved on Nov. 11, 2010] the whole document.
(Continued)

*Primary Examiner* — Amir Alavi

(57) ABSTRACT

Visualization of an object of interest, such as anatomy like a vessel segment or a stenosis, together with a device, such as balloon/stent markers or a wire tip, inside the object of interest may be accomplished by device detection and anatomy boosting so as to enhance both the device and surrounding anatomy within a registered anatomy referential. A displayed image is a combination of image information of the device and boosted image information of the object of interest. A processor performs the following steps: detecting and segmenting the device on the basis of image information provided by the image formation unit; either wiping out or attenuating the image information of the device; detecting the object of interest on the basis of the provided image information; boosting the image information of the object of interest; and reinserting the image information of the device.

20 Claims, 1 Drawing Sheet

(51) Int. Cl.
    *G06K 9/36*     (2006.01)
    *G06T 5/50*     (2006.01)
    *G06K 9/34*     (2006.01)
    *A61B 19/00*     (2006.01)

(52) U.S. Cl.
    CPC .................. *A61B 2019/5265* (2013.01); *G06T 2207/30021* (2013.01); *G06T 2207/10121* (2013.01); *G06T 2207/20224* (2013.01)

(56) References Cited

U.S. PATENT DOCUMENTS

| | | |
|---|---|---|
| 2007/0066899 A1 | 3/2007 | Boese et al. |
| 2007/0173861 A1 | 7/2007 | Strommer et al. |
| 2010/0026789 A1* | 2/2010 | Balogh ........................... 348/50 |
| 2011/0216092 A1* | 9/2011 | Florent ........................ 345/634 |
| 2012/0063657 A1* | 3/2012 | Ribbing et al. ............... 382/128 |

FOREIGN PATENT DOCUMENTS

| | | |
|---|---|---|
| WO | 2006114721 A2 | 11/2006 |
| WO | 2008081396 A2 | 7/2008 |

OTHER PUBLICATIONS

By Jorg Bredno et al; "Algorithmic Solutions for Live Device-To-Vessel Match" Philips Research Laboratories, Weisshausstrasse 2, D-52066 Aachen, Germany; Institute for Signal Processing, University of Lubeck, Ratzeburger Alle 160, D-235538 Lubeck; Medical Imaging 2004: Image Processing, edited by J. Michael Fitzpatric, Milan Sonka, Proceedings of SPIE vol. 5370; pp. 1486-1497.

Ross, "Registration and Integration for Fluoroscopy Device Enhancement", MICCAI, 2005, LNCS 3749, pp. 851-858.

* cited by examiner

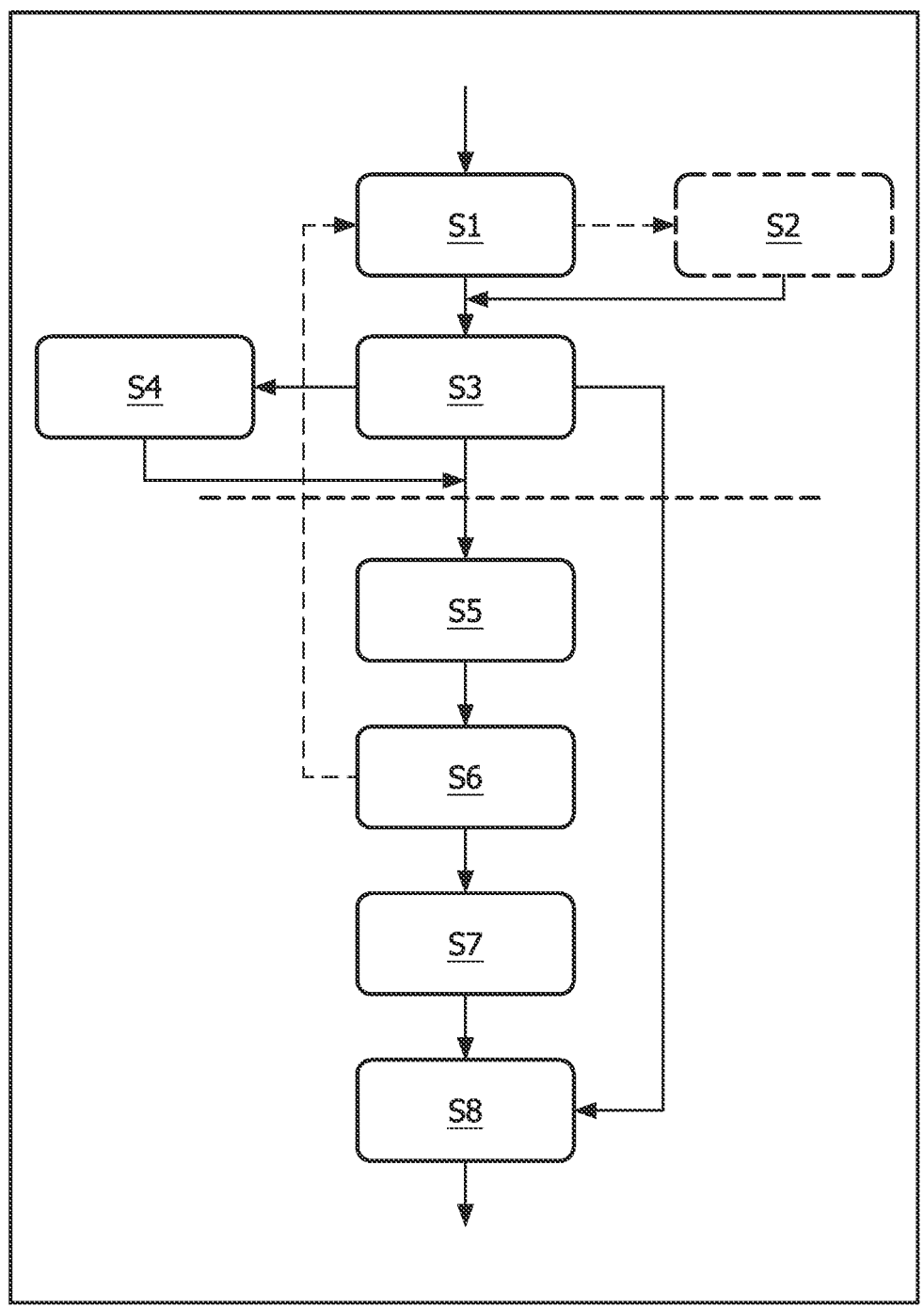

COMBINED DEVICE-AND-ANATOMY BOOSTING

This application is a 371 of PCT/IB09/54363 filed on Oct. 6, 2009.

Generally, the invention relates to an apparatus and a method for visualization of an object of interest together with a device being inside the object of interest. Further, the invention relates to the use of said apparatus as well as to a computer program product adapted for controlling the apparatus for visualization of an object of interest together with a device being inside the object of interest.

Particularly, the invention relates to an apparatus and a method for visualization of an anatomic structure together with a device used for treatment of a patient.

BACKGROUND OF THE INVENTION

A description of the basic interventional procedure which can be performed with an imaging system for 'Percutanerous Transluminal Coronary Angioplasty' (PTCA), to treat cardiac stenoses, can be found in "Algorithmic Solutions for Live Device-to-Vessel Match". J. Bredno, B. Martin-Leung & K. Eck. In Proceedings of SPIE—Volume 5370—Medical Imaging 2004: Image Processing, J. Michael Fitzpatrick, Milan Sonka, Editors, May 2004, pp. 1486-1497.

There is written: 'After a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries. Diagnosis and intervention planning are based on such diagnostic angiograms ( . . . ). During intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire ( . . . ) and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled.'

Now, one of the most delicate phases during PTCA is the passing of the guide-wire tip through the targeted lesion (stenosis). The vessel walls at this location are usually uneven, and by definition, the conduct is narrowed. It follows that stenosis passing is one of the most time consuming (and therefore dose generating) parts of the intervention.

Another delicate phase consists in positioning the balloon or stent markers with respect to the target lesion. The accuracy of this positioning is very important because it determines where the balloon and/or stent are to be deployed.

One of the reasons why the stenosis passing phase is difficult comes from the fact that it is achieved almost blindly and on a moving target. Most of the time, the cardiologist only sees the wire tip while trying to figure out what the stenosis looks like and what is the exact location of the tip within that stenosis. In this process, the cardiologist often injects a small shot of contrast agent to help figuring out where the tip is with respect to the stenosis, and then proceeds with the intervention. Likewise, when positioning the balloon/stent markers with respect to the stenosis, the cardiologist injects a small amount of contrast agent to determine how the markers should be moved to reach the optimal localisation.

In both cases (stenosis passing and marker positioning) contrast injection helps, but it still involves a difficult process because of a variety of factors including:

the presence of many motions (cardiac, respiratory, contrast agent flow, device), the fact that due to motion, zooming is limited, the poor contrast in the images due to the fluoroscopy conditions.

Now, in order to improve the situation, one can use a technique referred to as device boosting (see for instance "Registration and Integration for Fluoroscopy Device Enhancement". James C. Ross, David Langan, RaviManjeshwar, John Kaufhold, Joseph Manak, and David Wilson. Miccai 2005.), where one compensates for the device motion while enhancing the device visibility with temporal integration.

For device boosting, a viewing system performing an image processing method can be used. The viewing system comprises means for acquiring a sequence of images, and for processing and displaying said images in real time. The system comprises initialization means applied to the original images for extracting and localizing an object of interest, which may be moving with respect to the referential of the image, the background being moving both with respect to said referential and with respect to the object. The initialization means then comprise registration means for registering the object of interest with respect to the referential of the image. This system further comprises processing means for automatically enhancing the object of interest, for minimizing the noise and for blurring or fading the background of the images. Said processing means include at least a means for carrying out a temporal integration technique performed on at least two images where the object of interest has been registered with respect to the referential of the images. Since after registration of the object, the background still moves with respect to the referential of the images, this temporal integration technique provides an enhancement of the object of interest, while minimizing the noise and blurring and fading the background.

However, if the device moves with respect to the surrounding anatomy (which is usually the case for the applications presented above), then device-based registration and integration is bound to degrade the anatomy visibility (becoming blurred), and thus to degrade the device localisation with respect to this anatomy.

SUMMARY OF THE INVENTION

It is the purpose of the present invention to improve this situation and to offer a comfortable way to monitor both the device and an object of interest. In particular, it is essential to correctly visualize the moving device in a stabilized referential linked to the object of interest, with an enhanced view of both the device and the object of interest.

These and other aspects of the invention will be apparent from and elucidated with reference to the embodiment described hereinafter.

Generally, an apparatus and a method is proposed, for visualization of an object of interest together with a device being inside the object of interest. The apparatus comprises an image formation unit adapted for providing image information of the object of interest and the device, a processing unit and a display adapted for displaying the image, wherein the image is a combination of the image information of the device and the boosted image information of the object of interest. Here, the processing unit is adapted for performing the following steps: detecting and segmenting the device on the basis of image information provided by the image formation unit; wiping-out the image information of the device; registering the object of interest on the basis of the provided image information; boosting the image information of the object of interest; re-inserting the image information of the device.

The method according to the invention will be described in detail, later. Further according to the invention, the steps of the method can be stored as a computer program product controlling the apparatus to perform the steps of the method, on a computer readable medium.

In the following, the invention will be described by means of an exemplary embodiment with regard to the attached FIGURE.

FIG. 1 is a diagram showing schematically the steps of a method according to the invention.

It is proposed to combine a device-detection method and an anatomy boosting techniques in a way that leads to the enhancement of both the device (e.g. balloon/stent markers or wire-tip) and of the surrounding anatomy (e.g. stenosis) within a registered anatomy referential.

The essential feature of the invention consists in:

Automatically detecting and tracking the device (e.g. the markers or wire-tip),

Segmentation of the device, preferably after its boosting,

Determining the instant when contrast agent reaches the device's vicinity, making the anatomy (e.g. the stenosis) visible. This is done by monitoring the device contrast along time, Based on the device segmentation, applying a wiping-out method producing device-free images, Initiating anatomy registration around the detected device, but in the device-free data, Applying anatomy boosting, thus improving anatomy visibility and enabling registration (possibly involving elastic warping), Re-injecting the device (possibly independently boosted with the usual technique) in the registered anatomy referential.

As illustrated in FIG. 1, the proposed method relies on several steps, performed automatically and in every single fluoroscopy run, for example in a catheter based cardiologic intervention:

In step S1, a device is detected and tracked. This means, that the fluoroscopy run is analysed in real-time and the target device is detected (localised) and tracked. Because devices (markers and guide wire tip) are usually well identifiable, this procedure can be completely automated, requiring no (or very light) user interaction. For instance, for balloon/stent makers this procedure is already embedded within the stent boosting, as described above.

In step S2, as an optional task, a full device boosting can be achieved. Since detection and tracking are already achieved, this corresponds to temporal integration, plus spatial enhancing. After boosting, the signal-to-noise ratio of the device is improved, which facilitates the subsequent segmentation.

In step S3, the device is segmented. In step S1, the device was detected, that is accurately localised. But this does not necessarily mean it is segmented. For instance, in stent boosting, markers are accurately localised through their centroid, but they are not necessarily segmented. However, because of its strong signature, its available localisation, and because one can (optionally) rely on a boosted version of this device, usual techniques can be used to get a device segmentation. However, fuzzy segmentation (production of a device map where each value is representative of the probability of presence of the device) is also possible.

In step S4, a contrast agent is detected. Once the device is segmented (or simply localised and fuzzily represented), the contrast between the device and its vicinity is temporally analysed. This allows to monitor the arrival of the Contrast Agent and to automatically trigger the combined device-and-anatomy boosting procedure at an instant when anatomy detection and tracking is feasible (because sufficiently made visible by the Contrast Agent).

In step S5, the device is wiped-out or attenuated. Thanks to its segmentation, the device can be removed or attenuated, wherein segmentation simply means to get a device-map indicating, for each pixel, the probability of "deviceness" at this location. This can be achieved by standard so-called in-painting methods. However, the total device removal is not necessary, so that one can also achieve a device attenuation step thanks to a fuzzy segmentation (or device map).

In step S6, the object of interest is registered. Basically, the registration is the identification of the object of interest in a series of several images. This registration can be achieved by the detection of the object of interest and its tracking, or it can be achieved by direct motion vector field estimation in the vicinity of the device without explicit detection. Thanks to device localisation, the object of interest, usually the anatomy (vessel segment or stenosis), can be detected and tracked in the device free images (so that the device does not "gets in the way" of the anatomy detection algorithm). However, this is not necessary, and the anatomy might also be directly detected and tracked (thanks to device localisation information) in the original fluoroscopy images. It is interesting to remark that device detection and anatomy detection can be intimately coupled. The anatomy detection cannot be initiated without device localisation, but when this occurs, the contrast agent decreases the visibility of the device, while increasing the visibility of the anatomy. It might then be fruitful to use anatomy tracking information to feedback anatomy localisation information to device tracking in order to improve the performance of the latter (since the device is to be found close to—or more generally in spatial relation with—the anatomy).

In step S7, the object of interest is boosted. Once registered, the object of interest or the anatomy can be boosted, that is registered in an anatomy referential, then temporally integrated and spatially enhanced. This might involve elastic registration. Additional zooming is then of course possible.

In step S8, the device is re-injected. The device (segmented or fuzzily represented) can then be re-injected (with the correct geometrical transform) in the registered boosted anatomy sequence, thus producing a stabilized (possibly zoomed) sequence where both the anatomy and the device are enhanced, and the relative motions of which can be observed without any blurring.

As a result, a displayed image is achieved, showing boosted anatomy and device in the registered anatomy. Alternatively, on the display, the device and anatomy might be shown with their natural motion. In some applications it might even be advantageous to register the displayed image with respect to the device and to show the anatomy motion in a referential linked to the device.

According to other embodiments, fuzzy representation (device map) can be used instead of hard segmentation of the device and anatomy detection can occur without prior device wiping-out.

This invention might be applied in X-Ray cardiac systems for PCIs (Percutaneous Coronary Interventions). PCI is one of the most important applications of the Cardiac systems and the market is enormous. Reducing the intervention duration, reducing the necessary amount of dose and contrast agent, and increasing the procedure reliability and cardiologist's comfort are goals which are simultaneously met by the invention. In X-Ray, Electrophysiology interventions (Atrial ablation, or pace-maker placements) could also be potential applications.

Regarding other possible applications, any intervention imaging system can potentially be concerned. This is in particular the case in Ultrasound when biopsy is considered. The biopsy needle is the device, and it progresses into a possibly moving target organ. The organ might move because of the patient's breathing or motion, or because of the natural organ motion, or due to the interaction with the needle. For biopsy, it is also very desirable to see clearly the device and the targeted organ equally well, and to be able to figure out the relative motion of the needle with respect to the targeted organ.

While the invention has been illustrated and described in detail in the drawings and foregoing description, such illustration and description are to be considered illustrative or exemplary and. not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for visualization of an object of interest together with a device disposed inside the object of interest, the apparatus comprising:
   a processor configured for performing the following steps:
      detecting and segmenting the device on the basis of image information of the object of interest and the device;
      either wiping out or attenuating the image information of the device;
      registering of the object of interest on the basis of the provided image information;
      boosting the image information of the object of interest;
      reinserting the image information of the device in forming an image; and
   a display configured for displaying the image,
   wherein the image is a combination of the image information of the device and the boosted image information of the object of interest.

2. The apparatus of claim 1, further comprising an image formation unit configured for providing said image information on the basis of which said detecting and said segmenting are to occur.

3. The apparatus of claim 2, wherein the image formation unit is a computed tomography (CT) system, a magnetic resonance (MR) system, or an ultrasound system.

4. The apparatus of claim 1, wherein the registering of the object of interest includes detection of the object of interest and its tracking, or includes direct motion vector field estimation in the vicinity of the device.

5. The apparatus of any of claim 1, wherein the processor is configured for performing the further step of boosting the image information of the device.

6. The apparatus of claim 1, wherein the processor automatically performs the steps of respectively wiping out or attenuating the image information of the device, detecting the object of interest, boosting the image information of the object of interest, and reinserting the image information of the device, in case a contrast agent is detected by the processor.

7. The apparatus of claim 1, configured for said wiping out.

8. The apparatus of claim 1, configured for said attenuating.

9. The apparatus of claim 8, said attenuating comprising producing a device map whose entries are respectively representative of probabilities of presence of said device.

10. A method for visualization of an object of interest together with a device inside the object of interest, the method comprising the steps of:
   detecting and segmenting the device on the basis of the image information of the object of interest and of the device;
   either wiping out or attenuating the image information of the device;
   registering the object of interest on the basis of the image information;
   boosting the image information of the object of interest;
   reinserting the image information of the device; and
   displaying an image that is a combination of the boosted image information of the object of interest and the image information of the device.

11. The method of claim 10, wherein the registering of the object of interest includes detection of the object of interest and its tracking, or includes the direct motion vector field estimation in the vicinity of the device.

12. The method of claim 10, wherein the method includes the further step of boosting the image information of the device.

13. The method of claim 10, wherein the method includes the further step of detecting a contrast agent to trigger the steps of respectively wiping out or attenuating the image information of the device, detecting the object of interest, boosting the image information of the object of interest, and reinserting the image information of the device.

14. The method of claim 10, further comprising the step of, prior to the step of detecting and segmenting, providing said image information.

15. The method of claim 10, wherein the step of wiping out or attenuating wipes out said image information of the device.

16. The method of claim 10, wherein the step of wiping out or attenuating attenuates said image information of the device.

17. A non-transitory computer-readable medium embodying a program for visualization of an object of interest together with a device inside the object of interest, said program having instructions executable by a processor for performing a plurality of acts, among said plurality there being the acts of:
   detecting and segmenting the device on the basis of the image information of the object of interest and of the device;
   either wiping out or attenuating the image information of the device;

registering the object of interest on the basis of the image information;

boosting the image information of the object of interest;

reinserting the image information of the device; and displaying an image that is a combination of the boosted image information of the object of interest and the image information of the device.

18. The computer-readable medium of claim 17, said act of either wiping out or attenuating entailing said wiping out.

19. The computer-readable medium of claim 17, said act of either wiping out or attenuating entailing said attenuating.

20. The computer-readable medium of claim 19, said attenuating comprising producing a device map whose entries are respectively representative of probabilities of presence of said device.

* * * * *